United States Patent [19]

Wood et al.

[11] Patent Number: 4,676,237
[45] Date of Patent: Jun. 30, 1987

[54] INHALER DEVICE

[75] Inventors: John D. Wood, Cambridge; Julian M. Coles, Elsworth; William R. S. Baxter, Cambridge, all of England

[73] Assignee: Boutade Worldwide Investments NV, Netherlands Antilles

[21] Appl. No.: 821,597

[22] Filed: Jan. 23, 1986

[30] Foreign Application Priority Data

Jan. 29, 1985 [ZA] South Africa ............... 85/0679

[51] Int. Cl.[4] ........................................... A61M 15/00
[52] U.S. Cl. ........................... 128/203.17; 128/204.13; 128/204.14
[58] Field of Search .................. 128/203.17, 203.27, 128/204.13, 200.18, 200.21, 200.14; 261/104, 142, 153, 107, 154, DIG. 65, 78 A; 219/274, 272, 362; 122/366

[56] References Cited

U.S. PATENT DOCUMENTS

| 1,688,200 | 10/1928 | Morgenthaler | 219/274 |
| 3,431,393 | 3/1969 | Katsuda | 219/274 |
| 4,110,419 | 8/1978 | Miller | 128/204.13 |
| 4,263,907 | 4/1981 | Lindsey | 261/DIG. 65 |
| 4,419,302 | 12/1983 | Nishino et al. | 128/204.13 |
| 4,564,748 | 1/1986 | Gupton | 128/203.27 |

FOREIGN PATENT DOCUMENTS

| 0043041 | 9/1982 | Japan | 219/274 |
| 1294808 | 11/1972 | United Kingdom | 128/203.27 |

Primary Examiner—Henry J. Recla
Attorney, Agent, or Firm—McGlew and Tuttle

[57] ABSTRACT

An inhaler device which includes a wick which draws water from a reservoir and which is in contact with a heated plate. Air is directed over the heated wick surface by means of a fan thereby to produce a stream of heated humid air. A sensor monitors the temperature of the heated air stream and a control circuit which is responsive to the sensor maintains this temperature substantially constant at a predetermined value. The heated humid air stream is available for inhalation by a patient for the treatment of certain ailments.

7 Claims, 4 Drawing Figures

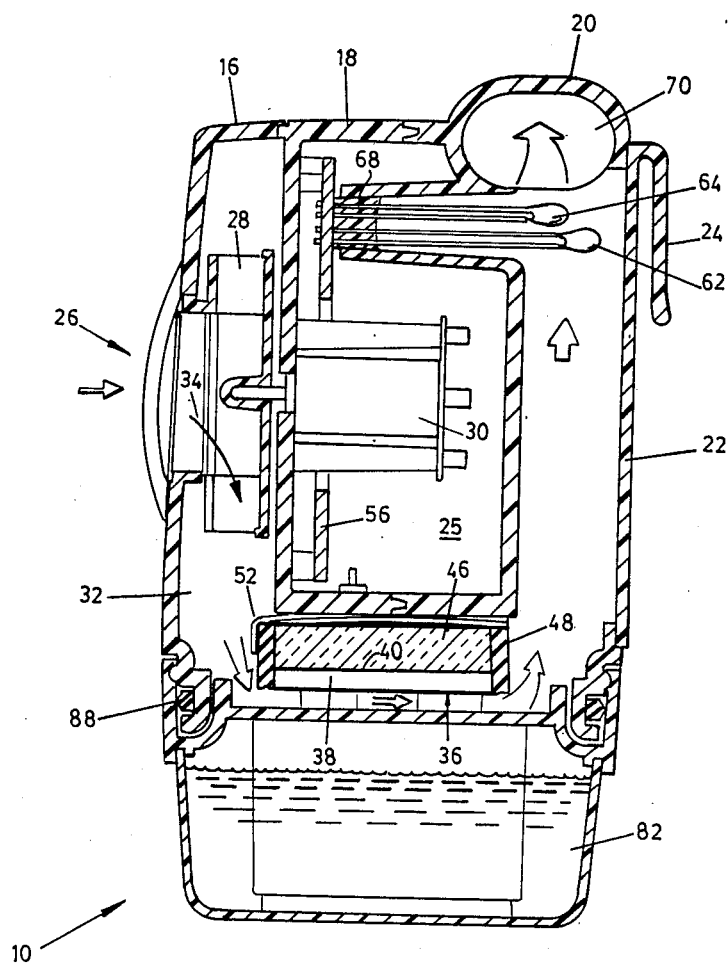
FIG_1

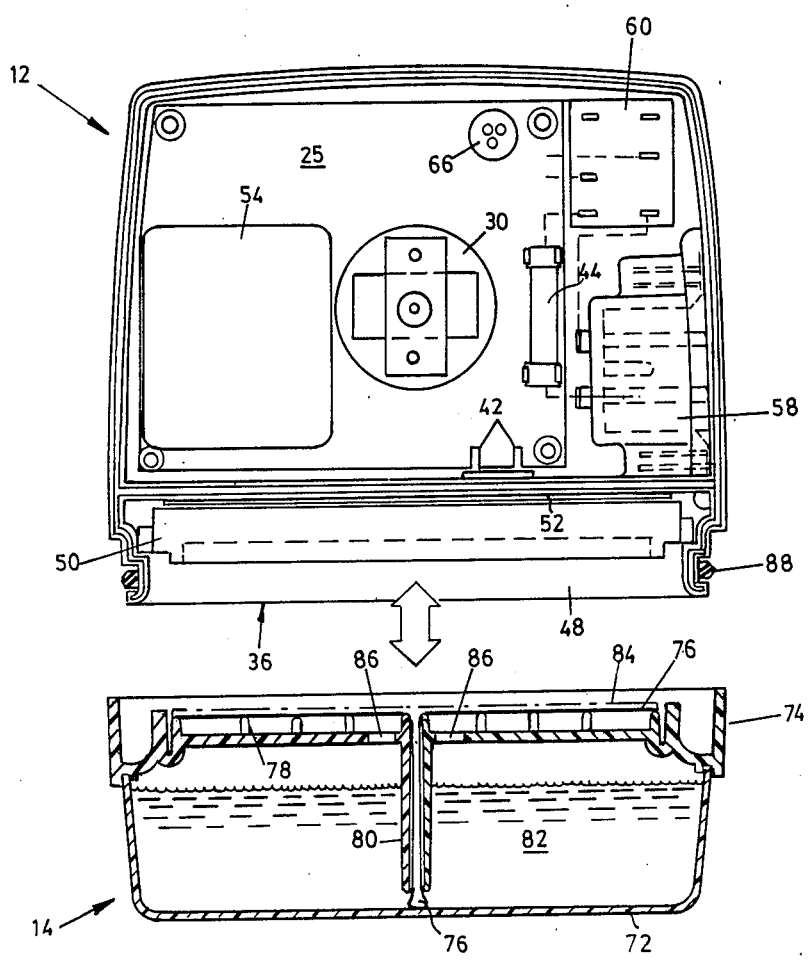
FIG_2

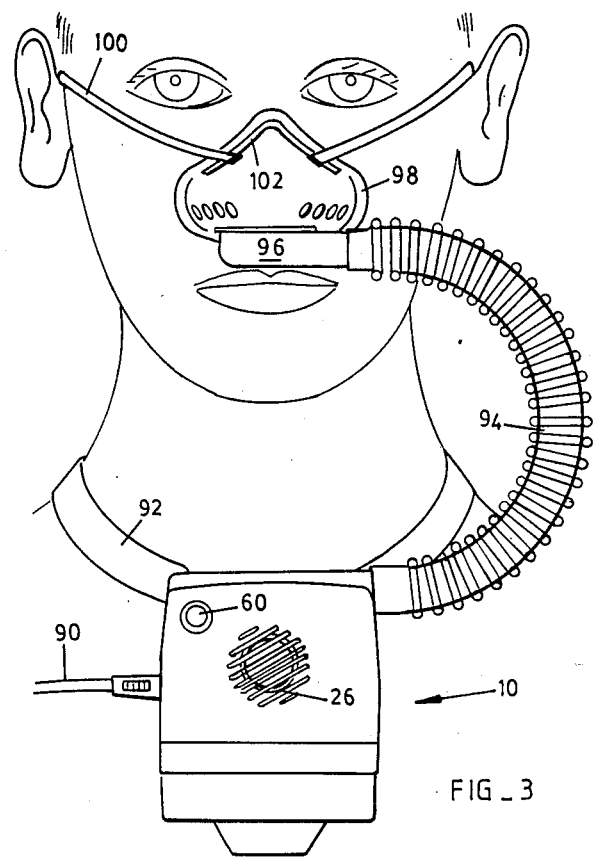
FIG_3

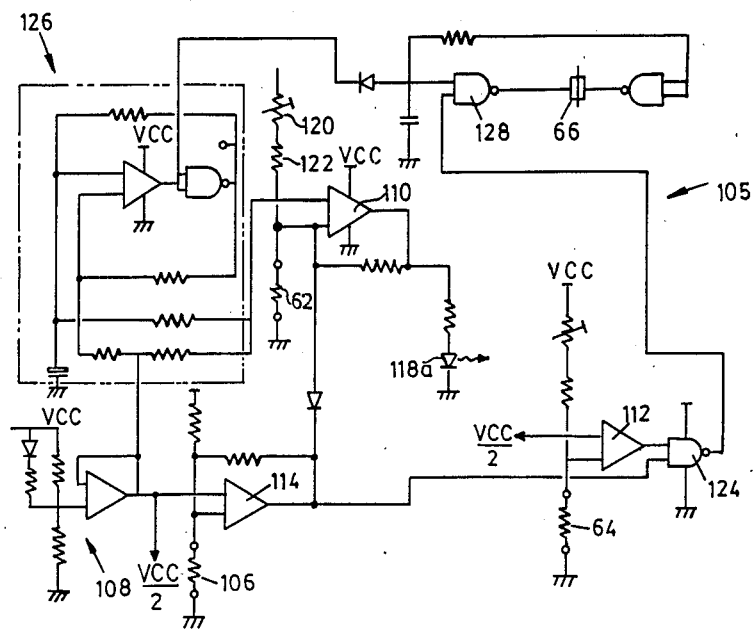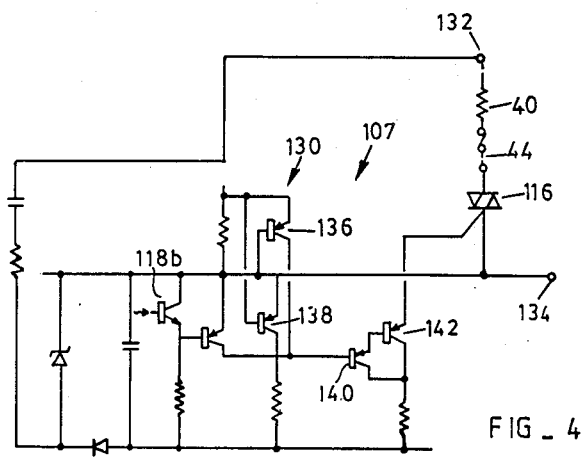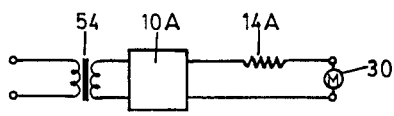
FIG_4

INHALER DEVICE

BACKGROUND OF THE INVENTION

This invention relates to an inhaler device.

It has been proposed to treat ailments such as the common cold by causing a patient to inhale heated humid air. It has been established through experimentation that the air temperature must be accurately controlled at a value of approximately 43° C. and that the relative humidity of the air should be at, or close to, saturation.

A large number of devices have previously been proposed for providing such a stream of air. Examples of these devices are disclosed in the specifications of the following patents: German Pat. Nos. 102693, 306287, 501505, 556493, 62252, 1233981, 1148355, 1933350, 2020435, 2160561, 2942631, 30259361 and 3139135; French Pat. Nos 727129, 783708, 914188, 2270897, 2276840, and 2440742; British Pat. Nos. 197946, 421708, 1435520, 1475710, 1490974, 1448473, 1343385, 1294808, 1242694, 1107780, 2010097A and 200238A; U.S. Pat. Nos. 631,575, 742,244, 865,021, 929,199, 155,419, 1,832,916, 2,040,630, 2,906,463, 2,151,719, 2,168,450, 2,174,531, 2,230,265, 2,233,431, 2,241,356, 2,262,711, 2,283,952, 2,366,753, 2,387,917, 2,445,347, 2,709,577, 3,190,502, 3,434,471, 3,506,003, 3,903,883, 3,990,441, 4,023,718 and 4,369,777; European Pat. No. 0.011847; Swiss Pat. No. 261779 and Austrian Pat. No. 150117.

SUMMARY OF THE INVENTION

It is an object of the present invention to provide an inhaler device for generating a stream of air at a predetermined temperature and relative humidity level which is lightweight and relatively easy to manufacture and which offers a high degree of safety in its use.

The invention provides an inhaler device which includes a housing which is formed with an air passage, a water reservoir, heater means, wick means which includes a section which extends into the water in the reservoir and a portion which is in heat exchanging contact with the heater means, means for directing an air stream through the air passage past the said portion of the wick means thereby to entrain moisture in the air stream and to heat the air stream, first means for sensing the temperature of the air stream at a given location which is downstream of the said portion of the wick means, and means responsive to the first temperature sensing means for varying the operation of the heater means thereby to maintain the temperature of the air stream, at the given location, substantially at a predetermined value.

The said portion of the wick means may be supported on a first side by means of a plurality of spaced formations and a second side of the said portion of the wick means may be in contact with an opposing surface of the heater means, the air stream being directed past the first side of the said portion of the wick means. Apart from not materially affecting the free flow of the air stream the formations provide a wick support that makes it possible to have a convenient detachable wicking system. These are significant advantages.

This arrangement means that the wick means, which is saturated with water, is heated by being in direct contact with the heater means and the water vapour which is released into the air stream is heated. The air stream is thus heated only by picking up hot water vapour and steam from the wick. The relative humidity in the air stream is therefore approximately 100%. Heating of the air stream directly by the heater is to be avoided, for the heat is "dry", and reduces the humidity level.

In a preferred form of the invention the reservoir is located at a lower end of the housing and the said portion of the wick means is positioned above the reservoir and below the heater means. However it is possible in variations of the invention to direct the air stream over an upper surface of a saturated wick. In a preferred variation substantially the whole of the heater means is covered by the wick means. Practically all of the heat is then taken up by the wick means, insulation requirements are reduced, and the heater can be smaller. The emission of "dry heat" into the air stream is also diminished.

The reservoir is preferably detachably engageable with the housing. The reservoir may be provided as a sealed unit, which contains distilled or demineralised water. A seal is removed from the reservoir by a user and the reservoir is then engaged with the housing so that the device is ready for use. In this variation of the invention the reservoir preferably includes a container, water in the container, support means above the water, wick means which includes a portion which is supported by the support means and a section which extends into the water in the reservoir, and detachable means overlying the wick means and sealing the container.

The heater means preferably includes a heating element and the means for varying the operation of the heater means includes switching means which controls the connection of the heating element to a source of electrical power in response to the first temperature sensing means.

A second temperature sensing means may be used for detecting a rise in the temperature of the air stream, at the given location, above an upper limit.

The depletion of water in the reservoir may be detected by means of a third temperature sensing means which is in contact with the heater means. When the water supply is exhausted the wick means is dried and no longer exerts a cooling action on the heater means. Consequently the temperature of the heater means rises and this can be detected by means of a suitable sensor. Similarly the sensor detects an attempt to operate the device when the resevoir is not in place.

The invention also extends to a method of providing a stream of heated humid air which includes the steps of heating at least a portion of a saturated wick, directing an air stream past the heated wick portion thereby to entrain moisture into the air stream, and to heat the air stream, sensing the temperature of the air stream downstream of the heated wick portion, and controlling the heating of the wick portion in response to the sensed temperature.

BRIEF DESCRIPTION OF THE DRAWINGS

The invention is further described by way of example with reference to the accompanying drawings in which:

FIG. 1 is a sectional side elevation of an inhaler device according to the invention, FIG. 2 is a view from the rear of the interior of the device shown in FIG. 1 with a reservoir, detached from an upper portion of the device, shown in section, FIG. 3 illustrates one way in which the device of FIGS. 1 and 2 is used, and FIG. 4 is a diagram of a circuit used for controlling the operation of the device shown in FIGS. 1 and 2.

DESCRIPTION OF PREFERRED EMBODIMENT

FIGS. 1 and 2 illustrate an inhaler device 10 according to the invention. The device includes a housing 12 and a detachable reservoir 14 which is engageable with a lower end of the housing. The housing 12 is made from four components and includes a fan cover 16, a front section 18, a rear section 20, and a rear cover 22. The cover 22 has a mounting clip 24 projecting from it. The front and rear sections 18 and 20 form an electronics compartment 25 between them.

The fan cover 16 has a partially shrouded air inlet opening 26 formed through it. A fan 28 which is driven by means of a motor 30 is mounted inside the housing so as to draw air through the opening 26 and expel it downwardly through an air passage 32 in the direction indicated by means of arrows 34. The fan operates centrifugally and creates an air flow of approximately 45 litres per minute through the air passage.

Mounted below the motor 30 and extending across the interior of the housing is a heating arrangement 36. This includes a ceramic heater plate 38 which is formed from 2 mm thick alumina with a heating element 40 being provided by a pattern printed in resistive ink on its upper surface. Terminals 42 which are connected to the heating element project upwardly into the electronics compartment inside the housing, see FIG. 2. One of these terminals is connected to a current fuse 44. The device in addition includes a thermal fuse, not shown, which provides protection in the event of normal control of the heating element being lost due to a faulty condition. The thermal fuse is mounted within the heater assembly 36, between the heater plate 38 and an insulating layer 46 of ceramic fibre which is 5 mm thick and which overlies the heater plate 38. This fuse is responsive to the temperature of the heater plate and it interrupts the supply to the heater element, in the event of a malfunction, if the temperature of the heater rises above a predetermined value.

The heater plate 38 and the insulating layer 46 are enclosed in a box 48 which is moulded in a heat resistant compound, to form a waterproof casing for the heating arrangement. The moulding includes projections 50 which engage with the housing thereby to retain the heating arrangement in position in the housing. The heater is also insulated on the air passage side to reduce the transfer of "dry heat" into the air stream.

A thin aluminium plate 52 is positioned between the heating arrangement and the electronics compartment 25. A portion of the plate, see FIG. 1, protrudes into the air passage 32 and thereby acts as a heat sink on the upstream side of the air passage relatively to the heating arrangement. This reduces the unwanted transfer of heat into the lower wall of the electronics compartment.

The electronics compartment includes a transformer 54 which is mounted on a printed circuit board 56 and which operates from a mains supply. The transformer provides power for the control circuit shown in FIG. 4. The mains supply is connected to a socket 58 which is internally wired via an on/off switch 60, the fuse 44 and the thermal fuse to the heating element 40, and to the electronic circuitry which is mounted on the printed circuit board 56.

Two encapsulated thermistors 62 and 64 respectively extend from the printed circuit board 56 into the air passage 32 adjacent the rear cover 22 of the device. The thermistor 62 is referred to as the main control thermistor and this determines, via the electronic circuit shown in FIG. 4, how much power is applied to the heater so as to achieve a desired operating condition. The second thermistor 64 is fitted for safety reasons and it detects an excess rise in air temperature in the passage 32. In the event of the air temperature increasing to an undesirable limit a warning buzzer 66, see FIG. 2, is activated. The thermistors are sealed on the printed circuit board 56 by means of a sealing compound 68.

The air passage on the rear side of the device terminates in an exit 70 which is substantially horizontal.

The reservoir 14 includes a container 72 with an upper moulding 74 which acts as a support for a wick 76. The support 74 includes a number of upstanding projections 78 which are spaced apart and which contact a lower surface of the wick thereby supporting the wick substantially horizontally. The support 74 includes a central downwardly extending projection 80 which is slotted and which engages with a central portion of the wick thereby enabling this central wick portion to extend to the bottom of the container 72.

The reservoir is intended to be disposable and it is supplied with approximately 70 ml of demineralised or distilled water 82. The wick takes up moisture from the water by capillary action. The wick is made from a non-woven viscose rayon.

The reservoir 14 is sealed by means of a foil cover 84 (shown chain dotted) which is attached to a lower perimeter of the support 74 and which is close fitting over the wick. This cover protects the wick prior to usage of the reservoir and ensures that water is not spilt from the container. The cover is removed before the reservoir is engaged with the upper portion of the inhaler device. The water in the reservoir is sterilised by gamma radiation.

The wick support 74 has vents 86 so positioned that spillage is avoided, when the container is full, if the container is tilted by up to 20° from the vertical.

When the reservoir 14 is engaged with the housing 12 a seal 88 prevents spillage of the water externally and also acts as an air seal.

FIG. 3 illustrates the device 10 in use. A power supply cord 90 is connected to the socket 58 on the housing. A strap 92 is engaged in a suitable way with the mounting clip 24, shown in FIG. 1, on the rear cover of the housing. The strap passes around the neck of a user. A flexible tube 94 is connected to the exit 70 from the air passage 32 and terminates in an adaptor piece 96 which diverts the air stream through 90° to allow it to impinge evenly on the nostrils of the user. The adaptor clips on to a mask 98 which is held in position over the nose of the user by means of an elastic strap 100 which is fixed to an aluminium strip 102 on the mask.

The operation of the inhaler device is under the control of the circuit shown in FIG. 4 which, as has previously been mentioned, is mounted on the printed circuit board 56 in the electronics compartment of the housing 12. The output from the transformer 54 is rectified by a bridge rectifier 104 and applied to the motor 30 and to a simple voltage smoothing circuit, not shown. The output of the smoothing circuit powers a thermistor monitoring circuit 105. A switching circuit 107 is used for controlling the supply of electrical power to the heater element 40.

The circuit 105 shows the main thermistor 62, the safety or second thermistor 64 and the buzzer 66. The circuit illustrates a third thermistor 106 which is not visible in FIGS. 1 and 2. This thermistor is a small chip which is attached to the upper surface of the ceramic heater plate 38 and which therefore monitors the temperature of this plate. The chip is of course electrically insulated from the heating element.

All the components shown in the circuit will not be described in detail for the nature of these components, and their method of operation, is apparent to those skilled in the art. However the aspects of the circuit which are essential for an understanding of the working of the inhaler device of the invention will be further elaborated on.

The stabilising circuit produces a voltage $V_{cc}$ which is applied to a reference circuit 108 which produces a reference voltage of $V_{cc}/2$ for all the control circuits.

The thermistor 62 is connected to a main control comparator 110. The thermistors 64 and 106 are similarly connected to comparators 112 and 114 respectively. The reference voltage $V_{cc}/2$ is applied to each of the comparators 110, 112 and 114.

The reference voltage to the main comparator 110 has a superimposed triangular wave with an amplitude which corresponds to a temperature variation of 3° C. This provides a proportional band in the control loop and gives an optimum transient response so that the operating temperature is reached as quickly as possible.

The heating element 40 is controlled via a triac 116 by the "burst fire" method. The triac, and hence the heater, is switched at a 1 Hz rate with a varying duty cycle depending on the power demand.

The heating element is controlled by the comparator 110 via an opto-isolator 118a and 118b. As indicated the reference voltage to the comparator 110 is a small amplitude triangular wave which is centered on the reference voltage $V_{cc}/2$. The other input to the comparator is a voltage derived from a potential divider formed by the thermistor 62 and resistors 120 and 122. The resistor 120 is variable and is set to provide the desired control temperature to which the air must be heated.

As the temperature of the thermistor 62 increases so does the voltage at the positive input to the comparator 110. Thus the duty cycle of the heating element, which is controlled by the output voltage of the comparator varies. Since this system is a feedback loop the circuit operates to maintain the thermistor at the resistance required for a duty cycle of about 60% and in this way the temperature is precisely controlled.

The comparator 110 is provided with a small amount of hysteresis to ensure clean switching of the comparator.

The heating element 40 is protected by means of the thermal fuse previously referred to. This fuse open circuits if the heater temperature rises excessively. Additional protection is provided for the heater, in the event of the reservoir 14 being depleted of water, by the thermistor 106 which is fixed to the heater. This thermistor controls the comparator 114 and if the temperature sensed by this thermistor rises above 140° C. the comparator switches so as to turn off the triac via the opto-isolator 118 and to turn on the buzzer 66 via an OR gate 124.

The comparator 114 has a large amount of hysteresis and consequently the heater has to cool considerably before it can again be turned on.

The thermistor 64 is designed to detect an excessive rise in the air temperature. If the air temperature in the passage 32 reaches 46° C. then the comparator 112 switches and the buzzer is again sounded.

It should be mentioned that the triangular wave which is applied to the reference input to the comparator 112 is produced by an oscillator 126 which functions at 1 Hz. This oscillator is also used to gate the buzzer 66 via an OR gate 128.

The triac 116 is driven by a transistor circuit 130. The main supply line is connected to terminals 132 and 134 in series with the heater and the triac.

The driver 130 includes transistors 136, 138, 140 and 142. The collector currents of the transistors 136 and 138 only drop to zero at zero crossings of the supply voltage. The transistors 140 and 142 then drive the triac. The triac has zero crossing triggering to keep radio interference to a minimum.

As indicated on/off switching of the triac is initiated via the opto-isolator 118. This increases the safety inherent in the circuit.

As a final feature of the circuit shown in FIG. 4 it should be pointed out that the speed of the motor 30 can be adjusted by means of a series resistor 144 to ensure that the correct rate of air flow is provided by the fan 28.

As has previously been indicated the inhaler device of the invention is intended to provide an air flow of approximately 45 litres per minute of heated humid air. The relative humidity of the air should be in excess of 70% and the temperature of the air should be accurately controlled at a value of approximately 43° C. The device functions as follows.

Air is drawn into the passage 32 by means of the fan 28 which is rotated by the motor 30. The air is directed downwardly in the passage 32 and passes below the undersurface of the wick 76 between the spaced projections 78. The air then travels upwardly past the thermistors 62 and 64 and leaves the housing via the air tube 94. The air is then presented to the user's nostrils where it is inhaled.

The wick 76 is kept in close contact with the heater plate 38 by the physical engagement of the housing and the reservoir. The wick is saturated at all times with water which is taken up by capillary action from the reservoir. As the wick is heated water vapour is given off into the volume between the wick support plate 74 and the wick and it is through this volume that the air passes. The air stream therefore entrains with it heated water vapour and is at the same time heated by coming into contact with the heater plate 38. The arrangement is such that the relative humidity of the air stream is considerably in excess of 70%.

The temperature of the air is monitored by the main thermistor 62 prior to leaving the housing 12. The control function provided by the circuit in response to the temperature which is sensed by the thermistor 62 is not a simple on/off operation responding to an air temperature above or below a set point. This approach does not provide the necessary accuracy and stability and consequently a proportional control technique is used. This works as follows. Around the desired temperature, say 43° C., there is a small temperature band referred to as a proportional band. When the temperature of the air is, say, halfway in this band the controller allows half the full power to flow, by letting half the AC main cycles through in a given time interval. The proportion of full power applied to the heater depends linearly on the air temperature within the proportional band, varying from zero when the air temperature is at the upper end of the temperature band to 100% when the air temperature is at the lower end of the band.

The heater element is controlled in this way so as to maintain the air temperature at the outlet at 43° C.±0.5° C.

The temperature band is however not centred on 43° C. because (a) the desired air temperature is reached typically when about three quarters of the full power is applied, and (b) the desired air temperature is 43° C., measured at the outlet, and there is a small temperature drop in the air as it travels along the tube 94 to the mask 96.

If the air temperature rises, because of a malfunction, to 46° C. this is sensed by the second or safety thermistor 64 and the buzzer 66 is sounded as a warning to the user.

If the water 82 in the reservoir 40 is depleted then the temperature of the heater plate rises as it is no longer subjected to the cooling effect of the wet wick. The thermistor 106 monitors the temperature of the heater plate and if this rises above 140° C., indicating that the water supply is exhausted, the buzzer 66 is sounded and the triac 116 is turned off in a manner analogous to that already described. Similar action occurs if the device is turned on when the reservoir is not coupled to the housing.

The close contact of the saturated wick portion with the heater plate provides a highly efficient way of raising the humidity level of the air stream and of simultaneously heating the air stream. The air stream should not be directly heated by the heater plate for this heat is dry and reduces the humidity level. It is to be noted that the wick presents a large area to the air stream, and the depth of the volume of space for the air flow is relatively small, and consequently the air stream is heated, and takes up moisture, substantially uniformly.

The circuit shown in FIG. 4 thus provides a control function to ensure that the temperature is kept constant at a desired value and in addition provides a monitoring function which advises the user when the water supply is exhausted or when the heater temperature increases excessively.

The device has being shown in FIG. 3 as providing an air stream for inhalation through the nose of a user. Clearly this system could be adapted to provide a mouth piece for oral inhalation.

The device of the invention is lightweight and easy to construct and use and offers a high degree of safety while at the same time providing an air stream of predetermined characteristics.

Various modifications can be made to the device without departing from the scope of this specification. For example the heating element could comprise a metal sheathed element with a heater core wire wound on mica. The socket 58 can be dispensed with and be replaced by a normal mains entry cable with a sheath. The exit 70 from the air passage could be at any other suitable orientation, for example vertical, to provide an appropriate connection point for the tube 94.

We claim:

1. An inhaler device which comprises a housing which is formed with an inlet and an outlet with an air passage therebetween, said housing having an open lower end, a water reservoir which is detachably engaged with the housing at the lower end thereof and which includes an upwardly facing cover which extends over the reservoir to cover water which may be filled into the reservoir and which has a plurality of spaced formations which extend upwardly from the cover to define air flow channels, heater means which includes a heater plate mounted in said housing adjacent the open lower end with a substantially flat and downwardly facing surface which opposes the cover of the water reservoir, wick means which includes a section which extends into the reservoir to be saturated with water in the reservoir and a portion having a downwardly facing first side and an upwardly facing second side and which is supported on the downwardly facing first side on the plurality of spaced formations which extend upwardly from the cover and with the upwardly facing second side in heat exchanging contact with the downwardly facing surface of the heater means, fan means mounted to the housing adjacent said inlet and means in said housing together with said fan means for directing an air stream into the housing inlet through the air passage and air flow channels defined by the downwardly facing first side of said portion of the wick means and above the cover of the water reservoir thereby to entrain moisture in the air stream and to heat the air stream and further to the housing outlet, first means for sensing the temperature of the air stream at a given location in said air passage which is downstream of said portion of the wick means, means responsive to the first temperature sensing means for varying the operation of the heater means thereby to maintain the temperature of the air stream, at a given location, substantially at a predetermined value, and means connected to the outlet of the air passage for conveying the heated and humidified air stream to the respiratory system of user.

2. Device of claim 1, wherein the heater means includes a heating element which is in oirect thermal contact with the heater plate, and the means for varying the operation of the heater means includes switching means which controls the connection of the heating element to a source of electrical power in response to the first temperature sensing means.

3. A device according to claim 1 which includes a second temperature sensing means for detecting a rise in the temperature of the air stream, at the given location, above an upper limit.

4. A device according to claim 1 which includes a third temperature sensing means, in contact with the heater means, for detecting when the water in the reservoir is depleted.

5. A disposable reservoir for use in a device intended for supplying temperature controlled, heated and humidified air, which comprises a sealable container providing a water-receiving space and having an open upper end adapted to be detachably engaged with a lower open end of a housing of such a device, support means forming a cover adjacent the upper end of the container and extending over the water-receiving space, a plurality of spaced formations extending upwardly from a portion of the cover defining air flow channels, wick means including a section which extends into the water-receiving space and a portion having a downwardly facing first side which is supported on the plurality of spaced formations to define air flow passages therethrough and an upwardly facing second side at the open upper end of the container.

6. Reservoir of claim 5 including water in the receiving space, and detachable means overlying the wick means and the portion of the cover at which the spaced formations are located and sealing the container at the open upper end thereof.

7. Reservoir of claim 6, wherein the so-sealed container is in sterilized condition.

* * * * *